US012766223B2

(12) United States Patent

Pei et al.

(10) Patent No.: US 12,766,223 B2
(45) Date of Patent: Oct. 20, 2026

(54) BIOCOMPATIBLE Mg-P COATING ON SURFACE OF ZINC- BASED BIOMEDICAL MATERIAL, AND PREPARATION METHOD AND USE THEREOF

(71) Applicant: SHANGHAI JIAO TONG UNIVERSITY, Shanghai (CN)

(72) Inventors: Jia Pei, Shanghai (CN); Boxuan Feng, Shanghai (CN); Ke Zhou, Shanghai (CN); Guangyin Yuan, Shanghai (CN)

(73) Assignee: SHANGHAI JIAO TONG UNIVERSITY, Shanghai (CN)

(*) Notice: Subject to any disclaimer, the term of this patent is extended or adjusted under 35 U.S.C. 154(b) by 1125 days.

(21) Appl. No.: 17/413,282

(22) PCT Filed: Jun. 28, 2020

(86) PCT No.: PCT/CN2020/098516
§ 371 (c)(1),
(2) Date: Jun. 11, 2021

(87) PCT Pub. No.: WO2021/057140
PCT Pub. Date: Apr. 1, 2021

(65) Prior Publication Data

US 2022/0023500 A1 Jan. 27, 2022

(30) Foreign Application Priority Data

Sep. 23, 2019 (CN) ......................... 201910899358.5

(51) Int. Cl.
*C23C 18/12* (2006.01)
*A61L 27/04* (2006.01)
(Continued)

(52) U.S. Cl.
CPC ............. *A61L 27/32* (2013.01); *A61L 27/047* (2013.01); *A61L 27/306* (2013.01); *A61L 27/54* (2013.01);
(Continued)

(58) Field of Classification Search
CPC .. C23C 18/04; C23C 18/1204; C23C 18/1241
See application file for complete search history.

(56) References Cited

U.S. PATENT DOCUMENTS

| | | | | |
|---|---|---|---|---|
| 6,136,369 A * | 10/2000 | Leitao | A61L 27/54 | 427/2.27 |
| 6,207,218 B1 * | 3/2001 | Layrolle | A61F 2/30767 | 427/2.27 |

(Continued)

FOREIGN PATENT DOCUMENTS

| | | |
|---|---|---|
| CN | 1169165 A | 12/1997 |
| CN | 1470672 A | 1/2004 |

(Continued)

OTHER PUBLICATIONS

Li, Huafang & Xie, Xin-Hui & Zheng, Yufeng & Cong, Yutian & Zhou, F. & Qiu, K. & Wang, Xinlei & Chen, Shihui & Huang, L. & Tian , L. & Qin, Linke. (2015). Development of biodegradable Zn—1X binary alloys with nutrient alloying elements Mg, Ca and Sr (vol. 5, 10719, 2015). Scientific Reports. 5. (Year: 2015).*

(Continued)

*Primary Examiner* — Dah-Wei D. Yuan
*Assistant Examiner* — Kristen A Dagenais
(74) *Attorney, Agent, or Firm* — Syncoda LLC; Feng Ma

(57) ABSTRACT

A biocompatible Mg—P coating on the surface of a zinc-based biomedical material, and a preparation method and use thereof are disclosed. In the method, zinc and a zinc alloy are first subjected to surface pretreatment and then soaked in a phosphate solution at a constant temperature to
(Continued)

form the Mg—P coating through chemical liquid deposition (CLD). The control on the composition, thickness and surface morphology of the coating is realized by using the CLD method. The biocompatible Mg—P coating has a thickness of 0.5 μm to 50 μm, is dense and uniform, and comprises a main component of zinc-magnesium-phosphate and a small amount of zinc phosphate.

8 Claims, 5 Drawing Sheets

(51) Int. Cl.

| | |
|---|---|
| ***A61L 27/30*** | (2006.01) |
| ***A61L 27/32*** | (2006.01) |
| ***A61L 27/54*** | (2006.01) |
| ***A61L 27/58*** | (2006.01) |
| ***A61L 31/02*** | (2006.01) |
| ***A61L 31/08*** | (2006.01) |
| ***A61L 31/14*** | (2006.01) |
| ***A61L 31/16*** | (2006.01) |
| ***C23C 18/04*** | (2006.01) |

(52) U.S. Cl.

CPC ............. *A61L 27/58* (2013.01); *A61L 31/022* (2013.01); *A61L 31/086* (2013.01); *A61L 31/088* (2013.01); *A61L 31/148* (2013.01); *A61L 31/16* (2013.01); *C23C 18/04* (2013.01); *C23C 18/1204* (2013.01); *C23C 18/1241* (2013.01); *A61L 2300/102* (2013.01); *A61L 2300/112* (2013.01); *A61L 2400/18* (2013.01); *A61L 2420/02* (2013.01); *A61L 2420/06* (2013.01); *A61L 2430/02* (2013.01)

(56) References Cited

U.S. PATENT DOCUMENTS

| | | | | |
|---|---|---|---|---|
| 2003/0236374 | A1* | 12/2003 | Bardman | C09D 133/04 526/274 |
| 2008/0177378 | A1* | 7/2008 | Asgari | A61L 27/427 623/1.38 |
| 2009/0246251 | A1* | 10/2009 | Orgambide | A61K 2300/00 424/93.1 |
| 2011/0184529 | A1* | 7/2011 | Forsgren | A61L 27/06 427/2.24 |
| 2017/0095358 | A1* | 4/2017 | Savage | A61L 31/148 |
| 2017/0326272 | A1* | 11/2017 | Harding | A61L 27/32 |

FOREIGN PATENT DOCUMENTS

| | | | |
|---|---|---|---|
| CN | 101376035 | A | 3/2009 |
| CN | 102727937 | A | 10/2012 |
| CN | 104212998 | A | 12/2014 |
| CN | 106913916 | A | 7/2017 |
| CN | 107456610 | A | 12/2017 |
| CN | 108853574 | A | 11/2018 |
| CN | 110448728 | A | 11/2019 |
| CN | 111218677 | A | 6/2020 |
| WO | 2016167460 | A1 | 10/2016 |
| WO | 2019002277 | A1 | 1/2019 |

OTHER PUBLICATIONS

Hou Yi, et al., Preparation and Characterization of Bioactive Mg—P Coating on the Biodegradable Porous Pure Zn Scaffold, Journal of Shanghai Jiao Tong University, 2019, pp. 521-528, vol. 53 No. 5.

* cited by examiner

BIOCOMPATIBLE Mg-P COATING ON SURFACE OF ZINC- BASED BIOMEDICAL MATERIAL, AND PREPARATION METHOD AND USE THEREOF

CROSS REFERENCE TO THE RELATED APPLICATIONS

This application is the national phase entry of International Application No. PCT/CN2020/098516, filed on Jun. 28, 2020, which is based upon and claims priority to Chinese Patent Application No. 201910899358.5, filed on Sep. 23, 2019, the entire contents of which are incorporated herein by reference.

TECHNICAL FIELD

The present invention belongs to the technical field of biomedical materials, and specifically relates to a biocompatible Mg—P coating on the surface of a zinc-based biomedical material, and a preparation method and use thereof.

BACKGROUND

Degradable medical metallic materials are a new type of biomedical materials that are gradually degradable after implanted in the body. In addition, upon their degradation they can produce products that will not trigger a severe host response and assist in tissue repair. Degradable magnesium alloys have been widely studied because magnesium ions can promote osteogenesis and can also promote endothelial cells (ECs) within a given concentration range, but the magnesium alloys are degraded at a high rate. As a new type of degradable medical metallic materials, zinc and zinc alloys show promising application prospects. Degradable zinc-based biomedical materials have at least two advantages:

1. Zinc is one of the important trace elements in the human body, which helps maintain the physiological functions of the human body and plays an important role in many enzyme reactions of an organism.
2. With a corrosion potential between that of magnesium and that of iron, zinc and zinc alloys corrode at a rate of tens of micrometers per year, which is much lower than that of magnesium and magnesium alloys (a few hundred micrometers per year).

From the perspective of the degradation time sequence-tissue function repair matching, zinc is an appropriate material for constructing degradable implants. The recommended daily allowance (RDA) of zinc is 2 mg to 10 mg, which is much higher than the amount of zinc ions released due to corrosion, indicating that zinc alloy implants do not cause excessive zinc intake. In addition, zinc-based implants show ideal degradation behaviors that are slow first and then fast in animals, and have a moderate overall degradation rate. Therefore, zinc and zinc alloys show high biological safety as degradable medical metallic materials.

Although the degradable zinc-based implants have the above-mentioned advantages and can be completely degraded after tissue function reconstruction or repair, avoiding secondary operations, there are still key problems to be solved for clinical applications. Common problems for pure zinc and reported zinc alloys include poor in vitro biocompatibility and cytotoxicity often at level 2 or even level 3 or 4, which cannot meet the requirements of clinical use. At present, experiments have shown that zinc ions degraded from degradable zinc-based implants show varying effects on ECs, smooth muscle cells (SMCs), and the like at varying concentrations. Generally, zinc at a low concentration can improve cell viability and promote cell proliferation, adhesion, and migration, while zinc at a too-high concentration shows strong in vitro cytotoxicity. The poor biocompatibility of degradable zinc-based implants is mainly due to the large cytotoxicity caused by excessively-high concentration of zinc ions (one of degradation products of the degradable zinc-based implants) locally released. Therefore, in order to ensure the normal migration, adhesion, proliferation, and differentiation of surrounding tissue cells on the surface of a zinc-based implant at an initial stage of implantation, it is necessary to control the initial corrosion of the zinc matrix and the initial release of zinc ions, thus improving the biocompatibility of the zinc-based implant.

Material surface modification provides a possible technical solution. However, related research is still at an early stage, and there are still few reports on surface modification or coatings that improve the biocompatibility of zinc materials. Recent studies have confirmed that micro-arc oxidation (MAO), polylactic acid (PLA) coating, and other common metal surface anti-corrosion treatment methods that are applied to the surface of medical magnesium alloys will promote the corrosion and degradation of a zinc matrix, which results in a higher concentration of locally-released zinc ions and thus further compromises the cell compatibility. There is only one report on gelatin coating modification that shows some improvement on EC adhesion, which is still inferior to the results of the negative control group. Phosphate is a common coating material for metal surface coating, but there is little report about using phosphate in the medical zinc-based surface modification.

Chinese patent CN1169165A discloses a method of coating a phosphate coating on a metal surface, including a method of coating a phosphate coating on the surface of a zinc alloy. According to this patented method, a substrate surface to be treated is allowed to contact with a phosphate solution by impregnating, flow-coating, or spray-coating to form a densely-bonded crystalline phosphate coating. The problem is that the solution includes nickel, manganese and other components, so that a finally obtained phosphate coating includes 0.5 wt. % to 3 wt. % of nickel, which is harmful to the human body.

Chinese patent CN1470672A discloses a zinc phosphate-containing surface conditioner, a steel plate treated through phosphate chemical conversion, a coated steel plate, and a zinc phosphate dispersion, including: forming a phosphate coating on the surface of a zinc alloy by impregnating in the zinc phosphate-containing surface conditioner, and so on. The problem is that the zinc phosphate-containing surface conditioner has a complicated composition and an optimal pH of 7 to 10, and zinc ions reach a saturated state and easily form precipitates in the form of zinc hydroxide under peralkaline conditions, so that the composition of a precipitated phosphate coating cannot be ensured and zinc hydroxide in the coating has poor biocompatibility.

Chinese patent CN201811409538.2 discloses a method for preparing a biologically-active calcium-phosphorus coating on the surface of a degradable medical zinc alloy. According to this method, a calcium-phosphorus coating is formed on the surface of a zinc alloy by chemical deposition. The main problem is that calcium salts, when used in implants such as vascular stents, can easily cause vascular calcification and affect the effect of stent implantation; and the calcium-phosphorus coating has a relatively rough surface morphology, which is difficult to adjust at a submicro-level.

SUMMARY

In view of the shortcomings in the prior art, the technical problem to be solved by the present invention is to provide a method for preparing a biocompatible Mg—P coating on the surface of a degradable zinc-based material. The coating is a composite conversion coating consisting of zinc-magnesium-phosphate and a small amount of zinc phosphate, which can be used in different applications by adjusting the kinetic and thermodynamic conditions to further deposit submicro-sized to micro-sized magnesium hydrogen phosphate particles on the surface of the coating. The preparation method specifically includes: preparing a biocompatible Mg—P coating on the surface of pretreated zinc and zinc alloy through chemical liquid deposition (CLD). The present invention designs a phosphate conversion coating doped with biologically-active magnesium. On the one hand, the dense coating serves as a barrier layer to reduce the initial corrosion of a zinc matrix and the initial release of the degradation product of zinc ions. On the other hand, the coating can also achieve the controllable and slow release of the biologically-active magnesium ions. The effects in the two aspects improve cell compatibility and biological activity of the surface of zinc and zinc alloys significantly and enhance biological functions of the zinc-based materials and medical devices. The process of the present invention is simple and easy to implement and requires no special equipment, a prepared coating is uniform and dense and shows complete coverage on and high bonding strength with a matrix, and the thickness and surface morphology of the coating can be adjusted.

The objective of the present invention is achieved by the following technical solutions.

The present invention provides a method for preparing a biocompatible Mg—P coating on the surface of a zinc-based biomedical material, including the following steps:

S1. pretreating the surface of the degradable zinc-based biomedical material, where, the pretreatment includes polishing, ultrasonic cleaning, and ultraviolet (UV)-ozone cleaning; and S2. soaking the degradable medical zinc alloy pretreated in step S1 in a slightly-acidic magnesium salt- and phosphate-containing solution at a constant temperature, and conducting CLD to obtain the biocompatible Mg—P coating.

The Mg—P coating prepared in the present invention can release an appropriate amount of biologically-active magnesium ions, which show a promoting effect on ECs and osteoblasts.

The biocompatible Mg—P coating provided in the present invention mainly has the following two advantages:

1. The zinc salt coating mainly exists in the form of zinc phosphate with a solubility product much smaller than that of other zinc salts, and the coating is dense and thus can serve as an effective corrosion barrier layer to significantly reduce the initial release of zinc ions, thereby improving the biocompatibility of medical zinc bases.
2. The coating is doped with biologically-active magnesium to achieve the controllable and slow release of magnesium ions, thereby further promoting the growth, differentiation, and the like of tissue cells such as ECs and osteoblasts.

Preferably, in step S2, the magnesium salt may be at least one selected from the group consisting of magnesium sulfate, magnesium nitrate, and magnesium phosphate, and the phosphate may be at least one selected from the group consisting of sodium phosphate, disodium phosphate (DSP), monosodium phosphate (MSP), potassium phosphate, dipotassium phosphate (DKP), and monopotassium phosphate (MKP).

Preferably, the magnesium salt- and phosphate-containing solution in step S2 may further include a solubilizing salt; and the solubilizing salt may include ethylene diamine tetraacetic acid (EDTA).

Preferably, the magnesium salt may have a concentration of 0.1 mol/L to 1 mol/L; the phosphate may have a concentration of 0.15 mol/L to 1.5 mol/L; and the magnesium salt and the phosphate may have a molar ratio range of 0.5-5. A too-high proportion of the magnesium salt will cause the formation and growth of large magnesium hydrogen phosphate particles on the coating surface; and a too-high proportion of the phosphate will cause the increase of a zinc phosphate content in the coating, which cannot effectively inhibit the initial release of zinc ions. Concentrations of the components in the solution in the range allow a uniform and dense Mg—P coating.

Preferably, in step S2, the constant-temperature soaking may be conducted at 10° C. to 80° C. for 0.5 h to 24 h, and the magnesium salt- and phosphate-containing solution may have a pH of 4.0 to 6.2. When the temperature is too low, the nucleation and growth of magnesium-phosphorus salt is too slow. When the temperature is too high, zinc is corroded too fast, which is not conducive to the growth and deposition of the coating; and a high temperature for a long time is also prone to affect the mechanical strength of a zinc matrix. When the soaking is conducted for a too-short time, the coating grows in an island-like manner and does not completely cover the surface of a matrix, and when the soaking is conducted for a too-long time, the reaction reaches equilibrium too early, and the thickness and composition of the coating basically no longer change. When the pH of the solution is too low, magnesium, zinc, and phosphorus mainly exist in the solution in respective ion forms, which is not conducive to the nucleation and growth in the reaction; and when the pH of the solution is too high, the magnesium and zinc ions reach a saturated state and are easily precipitated in the forms of magnesium hydroxide and zinc hydroxide.

Preferably, the ultrasonic cleaning in step S1 may include ultrasonic cleaning successively with absolute ethanol, acetone, and absolute ethanol.

Preferably, the degradable zinc-based biomedical material may be selected from the group consisting of pure Zn, Zn—Cu binary alloy, Zn—Mg binary alloy, Zn—Sr binary alloy, Zn—Mn binary alloy, Zn—Li binary alloy, Zn—Ag binary alloy, Zn—Fe binary alloy, Zn—Re binary alloy, and multi-element zinc alloy.

The present invention also provides a biocompatible Mg—P coating on the surface of a zinc-based biomedical material prepared by the method described above, and the biocompatible Mg—P coating has a thickness of 0.5 μm to 50 μm, is dense and uniform, and includes a main component of zinc-magnesium-phosphate and a small amount of zinc phosphate.

Preferably, an outer surface of the coating may further include submicro-sized to micro-sized magnesium hydrogen phosphate crystal grains.

The present invention also provides use of a degradable zinc-based biomedical material with the biocompatible Mg—P coating described above in the preparation of a biodegradable and absorbable medical device, and the medical device includes a tissue engineering scaffold, a cardiovascular stent, a medical catheter, and an intraosseous implant device.

The Mg—P coating prepared in the present invention shows complete coverage on and high bonding strength with a zinc and zinc alloy matrix, is uniform and dense, and can significantly reduce the initial corrosion of the zinc substrate and the initial release of zinc ions while releasing an appropriate amount of magnesium ions, which can improve the biocompatibility of degradable zinc-based implants. The CLD proposed by the present invention is simple, easy to implement, and low in cost, and requires no special equipment. The composition, thickness, and surface micromorphology of the coating can be adjusted by controlling the reaction conditions, thereby adjusting the initial release rate of zinc and magnesium ions and the response behaviors of tissue cells to the surface of a material. The present invention shows promising clinical application prospects in the fields of tissue engineering scaffolds, cardiovascular stents, medical catheters, and intraosseous implant devices.

Compared with the prior art, the present invention has the following beneficial effects.

5. The invention provides a method for preparing a biocompatible Mg—P coating on the surface of a degradable zinc-based biomedical material. The coating can significantly reduce the initial corrosion of a zinc matrix and the initial release of zinc ions while releasing an appropriate amount of biologically-active magnesium ions, thus improving the biocompatibility of degradable zinc-based biomedical materials.
6. The composition, morphology and thickness of the coating prepared by the present invention are controllable, and various coating structures for different medical applications can be synthesized by controlling and adjusting reaction conditions. The present invention can prepare a nano-sized, uniform, and dense thin-coating without micro-sized crystal grains on the surface, which is suitable for cardiovascular stents, medical catheters, and other fields. The present invention can also prepare a composite coating with micro-sized magnesium hydrogen phosphate crystal grains on the outer surface, which has the activity of promoting osteogenesis and is suitable for the fields such as intraosseous implant devices.
7. The CLD proposed by the present invention is simple, easy to implement, and low in cost, and requires no special equipment.
8. The invention is widely applicable and suitable for all pure zinc and zinc alloy materials and implant devices with any complex shape, such as tissue engineering scaffolds, cardiovascular stents, medical catheters, and intraosseous implant devices.

BRIEF DESCRIPTION OF THE DRAWINGS

Other features, objectives, and advantages of the present invention will become more apparent by reading the detailed description of non-limiting examples with reference to the following accompanying drawings.

DETAILED DESCRIPTION OF THE EMBODIMENTS

The present invention is described in detail below with reference to specific examples. The following examples will help those skilled in the art to further understand the present invention, but do not limit the present invention in any way. It should be noted that those of ordinary skill in the art can further make several variations and improvements without departing from the idea of the present invention. These all fall within the protection scope of the present invention.

Example 1

A biocompatible Mg—P coating was prepared on the surface of an extruded Zn-3 wt % Cu (Zn—Cu) alloy material. Specific steps were as follows:

4) The extruded Zn-3 wt % Cu alloy was made into a Φ10×3 mm sample, polished successively with 320 # and 1,200 # waterproof abrasive papers, then subjected to ultrasonic cleaning for 10 min successively with absolute ethanol, acetone, and absolute ethanol, and blow-dried, and then both sides of the sample were each treated for 10 min with a UV-ozone cleaner.

5) A phosphate reaction solution was prepared as follows: $MgSO_4$ and $NaH_2PO_4$ were taken at a ratio of 1:1.5 (a ratio of the amounts of the substances, 0.2 mol/L and 0.3 mol/L, respectively) and dissolved with deionized water, and a pH was adjusted to 4.0 with a 1 mol/L NaOH solution.

6) The treated Zn-3Cu alloy sample was statically soaked in the above phosphate reaction solution for 6 h at room temperature (25° C.).

Figure 1:
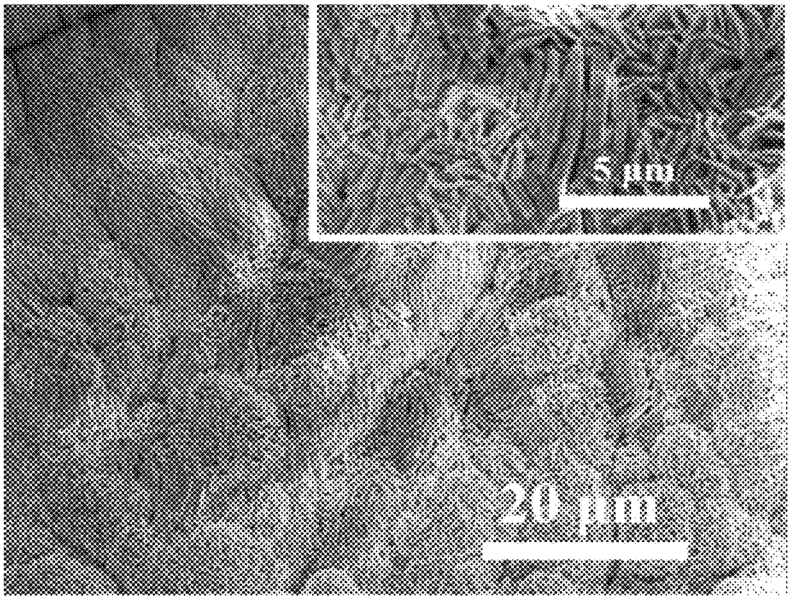
FIG. 1 is a scanning electron microscopy (SEM) image of the biocompatible Mg—P coating on the surface of a zinc alloy prepared in Example 1, with an enlarged image at the upper right corner. It can be seen from the figure that the surface of the coating has a micro-sized cluster-like morphology combined with a nano-sized rod-like structure and does not include micro-sized magnesium hydrogen phosphate particles.
Figure 2:
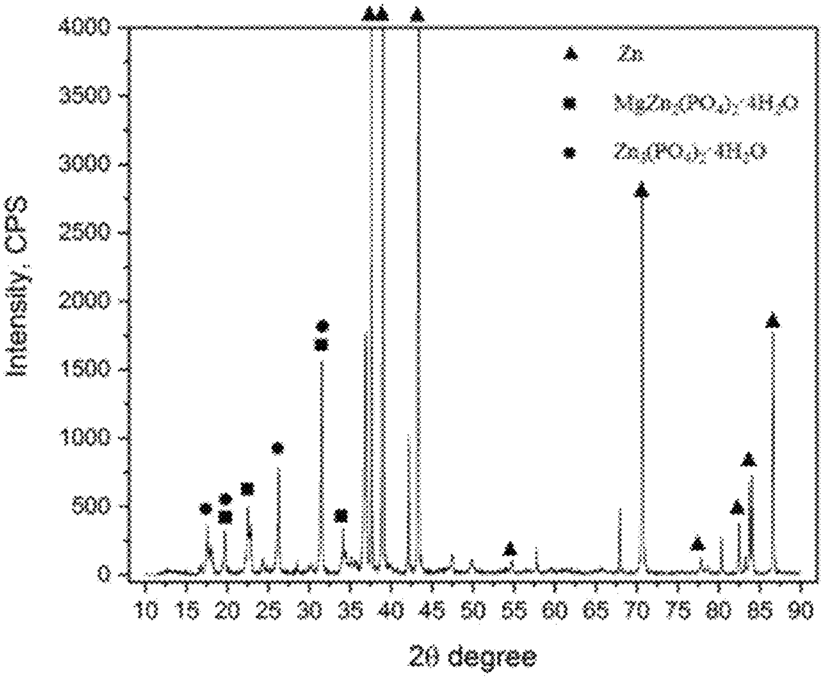
FIG. 2 shows an X-ray diffraction (XRD) pattern of the biocompatible Mg—P coating on the surface of a zinc alloy prepared in example 1, which verifies the main components of the coating.
Figure 6A:
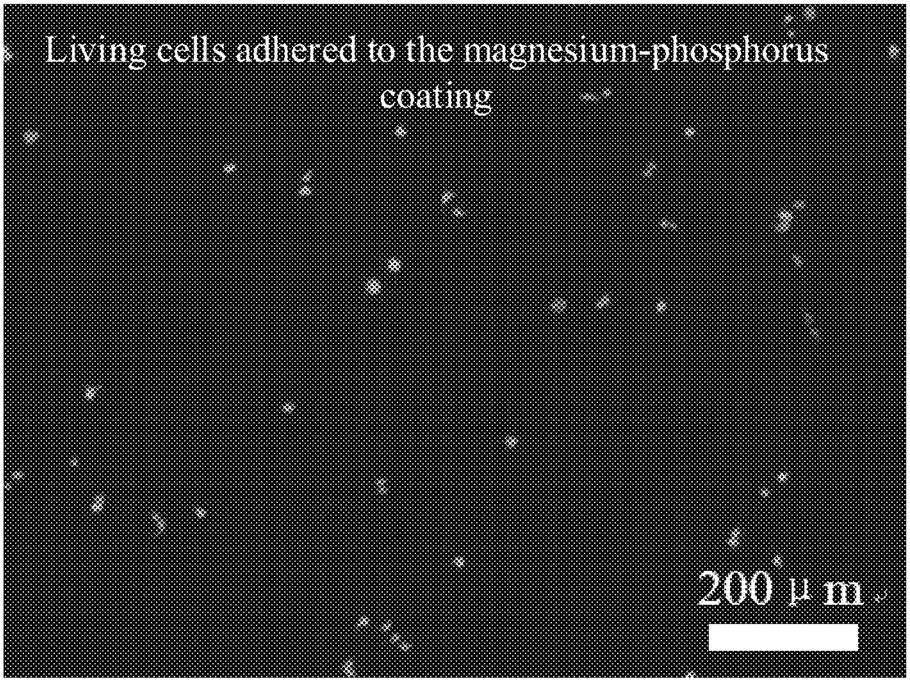
FIG. 6A is the fluorescence microscopy image of live cells of osteoblasts adhered to the biocompatible Mg—P coating on the surface of the zinc alloy prepared in Example 1.
Figure 6B:
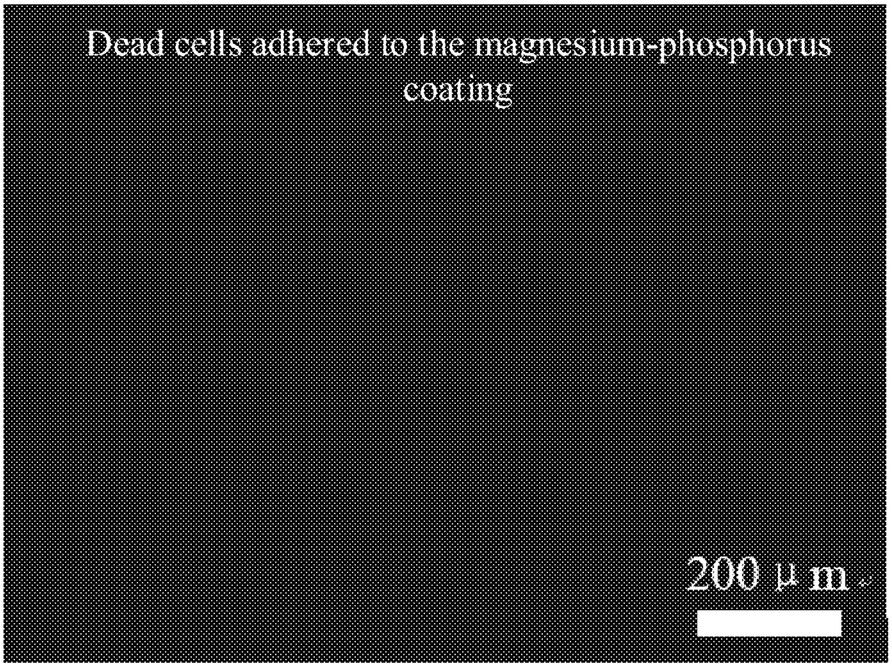
FIG. 6B is the fluorescence microscopy image of dead cells of osteoblasts adhered to the biocompatible Mg—P coating on the surface of the zinc alloy prepared in Example 1.
Figure 6C:
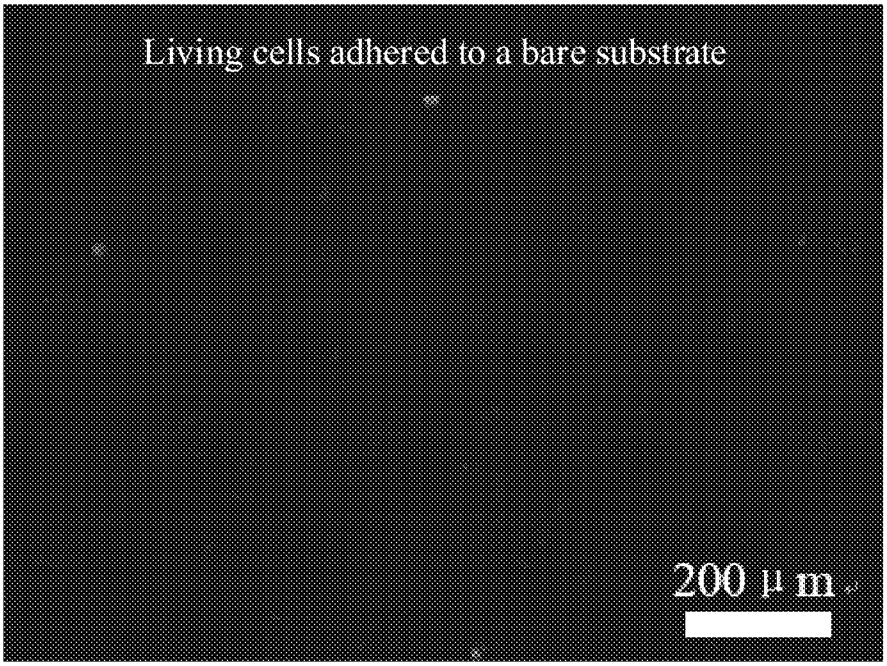
FIG. 6C is the fluorescence microscopy image of live cells on the bare zinc alloy in the control group.
Figure 6D:
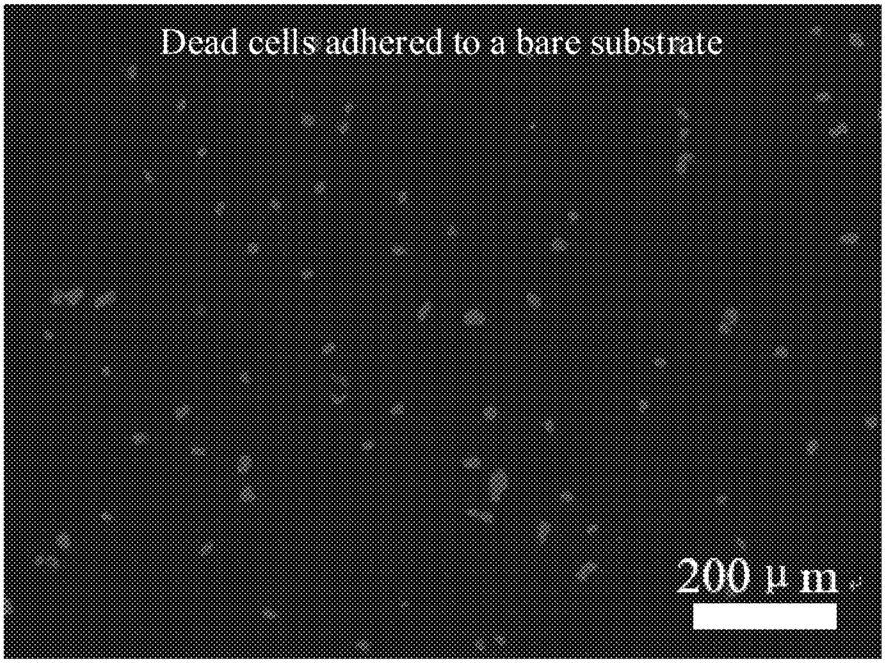
FIG. 6D is the fluorescence microscopy image of dead cells of the bare zinc alloy in the control group; it can be seen that the cells adhered to the modified Mg—P coating show a significantly-improved survival rate.

As shown in the SEM image (as shown in FIG. 1), the surface of the coating had a micro-sized cluster-like morphology combined with a nano-sized rod-like structure and did not include micro-sized magnesium hydrogen phosphate particles. It was also observed that the Mg—P coating had a thickness of about 10 μm, a Mg/Zn/P atomic ratio of about 1:2:2, and a bonding force as high as 10 MPa with the Zn-3Cu alloy matrix. The Mg—P coating prepared in this example, after soaked in a α-MEM medium for one week, showed a zinc release rate reduced to 10% of that of a bare Zn-3Cu alloy, and could release an appropriate amount of magnesium ions at the same time. The EA. Hy926 ECs were used to evaluate the biocompatibility of the Mg—P coating prepared in this example, and results showed that a large number of spreading ECs were adhered to the surface of the Mg—P coating and the coating exhibited cytotoxicity reduced from level 2 to level 0, indicating that the Mg—P coating can promote the spreading, adhesion, and proliferation of ECs and significantly improves the cell compatibility of the zinc alloy surface. An XRD pattern of the biocompatible Mg—P coating on the surface of the zinc alloy prepared in this example is shown in FIG. 2. Fluorescence microscopy images for the live/dead staining of osteoblasts adhered to the biocompatible Mg—P coating on the surface of the zinc alloy are shown in FIGS. 6A-B, and compared with fluorescence microscopy images for the live/dead staining of cells adhered to the bare zinc alloy in the control group (as shown in FIGS. 6C-D), it can be seen that adhered cells have a significantly-improved survival rate after modification with the Mg—P coating. The coating process in this example is suitable for the preparation of a surface coating for vascular stents manufactured from the Zn-3Cu alloy.

Example 2

A biocompatible Mg—P coating was prepared on the surface of a Zn—Mg alloy porous bone tissue engineering scaffold for tissue engineering. Specific steps were as follows:

4) The Zn—Mg alloy porous bone tissue engineering scaffold for tissue engineering was made into a Φ10×3 mm sample, then the porous surface was polished by electrolytic polishing, and a resulting sample was subjected to ultrasonic cleaning for 10 min successively with absolute ethanol, acetone, and absolute ethanol, blow-dried, and then treated for 10 min with a UV-ozone cleaner.

5) A phosphate reaction solution was prepared as follows: $MgSO_4$ and $NaH_2PO_4$ were taken at a ratio of 1:1.5 (a ratio of the amounts of the substances, 0.2 mol/L and 0.3 mol/L, respectively) and dissolved with deionized water, and a pH was adjusted to 5.0 with a 1 mol/L NaOH solution.

6) The treated Zn—Mg alloy porous bone tissue engineering scaffold sample was put in the above phosphate reaction solution, and static soaking was conducted for 12 h in a water bath at a constant temperature (50° C.).

It was observed from SEM that the Mg—P coating had a total thickness of about 30 μm and a Mg/Zn/P atomic ratio of about 1:2:2; the micro-sized crystal grains on the coating surface had a Mg/P atomic ratio of about 1:1 and basically included no Zn atoms; and there was a bonding force as high as 8 MPa between the coating and the Zn—Mg alloy porous bone tissue engineering scaffold matrix. The Mg—P coating prepared in this example, after soaked in a α-MEM medium for one week, showed a zinc release rate reduced to 11% of that of a bare Zn—Mg alloy porous bone tissue engineering scaffold, and could release an appropriate amount of magnesium ions at the same time. The MC3T3-E1 osteoblasts were used to evaluate the biocompatibility of the Mg—P coating prepared in this example, and results showed that a large number of spreading osteoblasts were adhered to the surface of the Mg—P coating and the coating exhibited cytotoxicity reduced from level 2 to level 0, indicating that the Mg—P coating can promote the spreading, adhesion, and proliferation of osteoblasts and significantly improves the cell compatibility of the zinc alloy tissue engineering scaffold surface.

Example 3

A biocompatible Mg—P coating was prepared on the surface of a cardiovascular stent manufactured from a Zn—Mn alloy. Specific steps were as follows:

4) The Zn—Mn alloy was made into a Φ3×15 mm sample, then the surface was polished by electrolytic polishing, and a resulting sample was subjected to ultrasonic cleaning for 10 min successively with absolute ethanol, acetone, and absolute ethanol, blow-dried, and then treated for 10 min with a UV-ozone cleaner.

5) A phosphate reaction solution was prepared as follows: $MgSO_4$ and $NaH_2PO_4$ were taken at a ratio of 1:1.5 (a ratio of the amounts of the substances, 0.3 mol/L and 0.45 mol/L, respectively) and dissolved with deionized water, and a pH was adjusted to 4.0 with a 1 mol/L NaOH solution.

6) The treated Zn—Mn alloy cardiovascular stent sample was statically soaked in the above phosphate reaction solution for 1 h at room temperature (25° C.).

It was observed from SEM that the Mg—P coating had a thickness of about 1.5 μm and a Mg/Zn/P atomic ratio of about 1:2:2; and there was a bonding force as high as 10 MPa between the coating and the Zn—Mn alloy cardiovascular stent matrix. The Mg—P coating prepared in this example, after soaked in a α-MEM medium for one week, showed a zinc release rate reduced to 12% of that of a bare Zn—Mn alloy stent, and could release an appropriate amount of magnesium ions at the same time. The EA. Hy926 ECs were used to evaluate the biocompatibility of the Mg—P coating prepared in this example, and results showed that a large number of spreading ECs were adhered to the surface of the Mg—P coating and the coating exhibited cytotoxicity reduced from level 2 to level 0, indicating that the Mg—P coating can promote the spreading, adhesion, and proliferation of ECs and significantly improves the cell compatibility of the zinc alloy stent surface.

Example 4

A biocompatible Mg—P coating was prepared on the surface of a Zn—Cu—Fe alloy bone nail. Specific steps were as follows:

4) The Zn—Cu—Fe alloy was made into a Φ4×10 mm bone nail sample, then the surface was polished by sand blasting, and a resulting sample was subjected to ultrasonic cleaning for 10 min successively with absolute ethanol, acetone, and absolute ethanol, blow-dried, and then treated for 10 min with a UV-ozone cleaner.

5) A phosphate reaction solution was prepared as follows: $MgSO_4$ and $NaH_2PO_4$ were taken at a ratio of 1:1.5 (a ratio of the amounts of the substances, 0.2 mol/L and 0.3 mol/L, respectively) and dissolved with deionized water, and a pH was adjusted to 6.0 with a 1 mol/L NaOH solution.

6) The treated Zn—Cu—Fe alloy sample was put in the above phosphate reaction solution, and static soaking was conducted for 2.5 h in a water bath at a constant temperature (35° C.).

It was observed from SEM that the Mg—P coating had a total thickness of about 15 μm and a Mg/Zn/P atomic ratio of about 1:2:2; the micro-sized crystal grains on the coating surface had a Mg/P atomic ratio of about 1:1 and basically included no Zn atoms; and there was a bonding force as high as 8 MPa between the coating and the Zn—Cu—Fe alloy matrix. The Mg—P coating prepared in this example, after soaked in a α-MEM medium for one week, showed a zinc release rate reduced to 11% of that of a bare Zn—Cu—Fe alloy, and could release an appropriate amount of magnesium ions at the same time. The MC3T3-E1 osteoblasts were used to evaluate the biocompatibility of the Mg—P coating prepared in this example, and results showed that a large number of spreading osteoblasts were adhered to the surface of the Mg—P coating and the coating exhibited cytotoxicity reduced from level 2 to level 0, indicating that the Mg—P coating can promote the spreading, adhesion, and proliferation of osteoblasts and significantly improves the cell compatibility of the zinc alloy bone nail surface.

Example 5

A biocompatible Mg—P coating was prepared on the surface of an intramedullary pin sample (Φ2×100 mm) manufactured from an extruded Zn-1Ag (Zn—Ag) alloy. Specific steps were as follows:

4) The extruded Zn-1Ag alloy was made into a 02×100 mm sample, polished successively with 320 # and 1,200 # waterproof abrasive papers, then subjected to ultrasonic cleaning for 10 min successively with absolute ethanol, acetone, and absolute ethanol, blow-dried, and then treated for 10 min with a UV-ozone cleaner.

5) A phosphate reaction solution was prepared as follows: $MgSO_4$ and $NaH_2PO_4$ were taken at a ratio of 1:1.5 (a ratio of the amounts of the substances, 0.3 mol/L and 0.45 mol/L, respectively) and dissolved with deionized water, and a pH was adjusted to 4.9 with a 1 mol/L NaOH solution.

6) The treated Zn-1Ag alloy sample was put in the above phosphate reaction solution, and static soaking was conducted for 6 h in a water bath at a constant temperature (50° C.).

It was observed from SEM that the Mg—P coating had a total thickness of about 8 μm and a Mg/Zn/P atomic ratio of about 1:2:2; the micro-sized crystal grains on the coating surface had a Mg/P atomic ratio of about 1:1 and basically included no Zn atoms; and there was a bonding force as high as 8 MPa between the coating and the Zn-1Ag alloy matrix. The Mg—P coating prepared in this example, after soaked in a α-MEM medium for one week, showed a zinc release rate reduced to 10% of that of a bare Zn-1Ag alloy, and could release an appropriate amount of magnesium ions at the same time. The MC3T3-E1 osteoblasts were used to evaluate the biocompatibility of the Mg—P coating prepared in this example, and results showed that a large number of spreading osteoblasts were adhered to the surface of the Mg—P coating and the coating exhibited cytotoxicity reduced from level 2 to level 0, indicating that the Mg—P coating can promote the spreading, adhesion, and proliferation of osteoblasts and significantly improves the cell compatibility of the zinc alloy intramedullary pin surface.

Example 6

A biocompatible Mg—P coating was prepared on the surface of a bone plate manufactured from pure zinc. Specific steps were as follows:

4) The pure zinc was made into a Φ10×3 mm sample, polished successively with 320 # and 1,200 # waterproof abrasive papers, then subjected to ultrasonic cleaning for 10 min successively with absolute ethanol, acetone, and absolute ethanol, and blow-dried, and then both sides of the sample were each treated for 10 min with a UV-ozone cleaner.

5) A phosphate reaction solution was prepared as follows: $MgSO_4$ and $NaH_2PO_4$ were taken at a ratio of 1:1.5 (a ratio of the amounts of the substances, 0.2 mol/L and 0.3 mol/L, respectively) and dissolved with deionized water, and a pH was adjusted to 4.0 with a 1 mol/L NaOH solution.

6) The treated pure zinc sample was statically soaked in the above phosphate reaction solution for 20 h at room temperature (25° C.).

Figure 3:
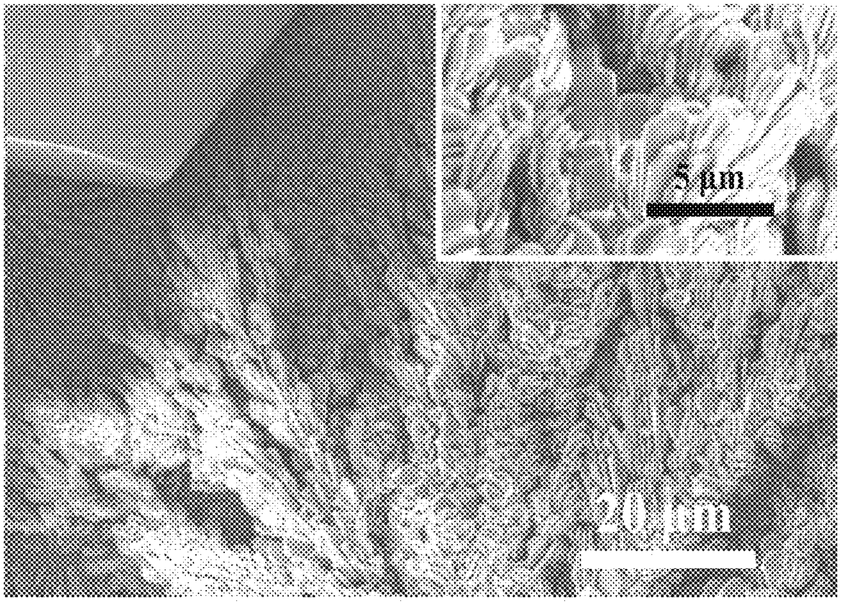
FIG. 3 is an SEM image of the biocompatible Mg—P coating on the surface of pure zinc prepared in Example 6, with an enlarged image at the upper right corner. It can be seen from the figure that the surface of the coating has a micro-sized cluster-like morphology combined with a nano-sized rod-like structure and includes micro-sized magnesium hydrogen phosphate particles.
Figure 4:
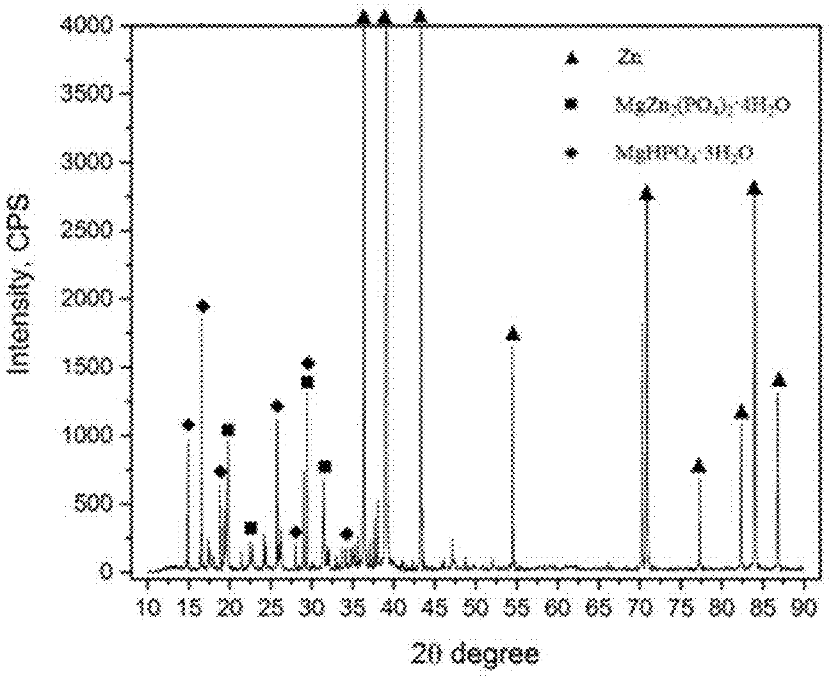
FIG. 4 shows an XRD pattern of the biocompatible Mg—P coating on the surface of pure zinc prepared in example 6, which verifies the main components of the coating.
Figure 5:
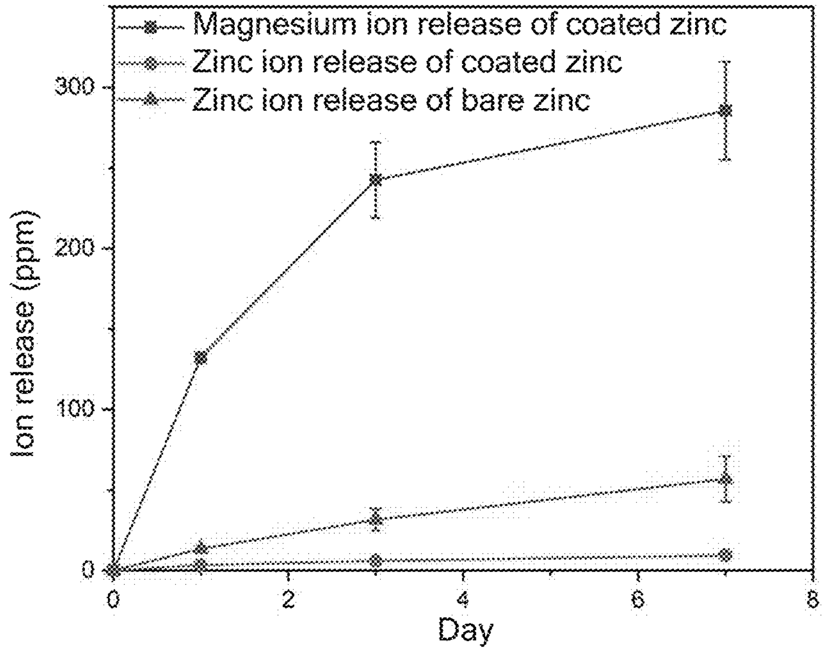
FIG. 5 shows the release curves of zinc and magnesium ions of the pure zinc with the biocompatible Mg—P coating prepared in Example 6 and the uncoated bare pure zinc in a cell culture medium. It can be seen that, within one week, the pure zinc with the biocompatible Mg—P coating prepared in Example 6 releases zinc ions at a significantly-reduced amount during degradation and can release an appropriate amount of magnesium ions at the same time, which is beneficial to improving the biocompatibility and biological activity of a zinc-based material surface.

It was observed from SEM (FIG. 3) that the surface of the coating had a micro-sized cluster-like morphology combined with a nano-sized rod-like structure and included micro-sized magnesium hydrogen phosphate particles. The Mg—P coating had a thickness of about 45 μm and a Mg/Zn/P atomic ratio of about 1:2:2; and there was a bonding force as high as 10 MPa between the coating and the pure zinc matrix. The Mg—P coating prepared in this example, after soaked in a α-MEM medium for one week, showed a zinc release rate reduced to 10% of that of bare pure zinc, and could release an appropriate amount of magnesium ions at the same time. The EA. Hy926 ECs were used to evaluate the biocompatibility of the Mg—P coating prepared in this example, and results showed that a large number of spreading ECs were adhered to the surface of the Mg—P coating and the coating exhibited cytotoxicity reduced from level 2 to level 0, indicating that the Mg—P coating can promote the spreading, adhesion, and proliferation of ECs and significantly improves the cell compatibility of the pure zinc bone plate surface. An XRD pattern of the biocompatible Mg—P coating on the surface of pure zinc prepared in this example is shown in FIG. 4. The release curves of zinc and magnesium ions of the pure zinc with the biocompatible Mg—P coating prepared in this example in a cell culture medium are shown in FIG. 5. It can be seen that, within one week, compared with bare pure zinc without coating, the pure zinc with the biocompatible Mg—P coating prepared in Example 6 releases zinc ions at a significantly-reduced amount during degradation and can release an appropriate amount of magnesium ions at the same time, which is beneficial to improving the biocompatibility and biological activity of a zinc-based material surface.

Example 7

A biocompatible Mg—P coating was prepared on the surface of an extruded Zn-3 wt % Cu (Zn—Cu) alloy material. The specific steps in this example were basically the same as Example 1 except that:

In step 2), a phosphate reaction solution in this example was prepared specifically as follows: $MgSO_4$ and $NaH_2PO_4$ were taken at a ratio of 0.5:1 (a ratio of the amounts of the substances, 0.1 mol/L and 0.2 mol/L, respectively) and dissolved with deionized water, and a pH was adjusted to 6.2 with a 1 mol/L NaOH solution.

In step 3), the treated Zn-3Cu alloy sample was statically soaked in the above phosphate reaction solution for 24 h at 10° C. in this example.

It was observed from SEM that the Mg—P coating had a thickness of about 20 μm and a Mg/Zn/P atomic ratio of about 1:2:2; and there was a bonding force as high as 8 MPa between the coating and the Zn-3Cu alloy matrix. The Mg—P coating prepared in this example, after soaked in a DMEM medium for one week, showed a zinc release rate reduced to 12% of that of a bare Zn-3Cu alloy, and could release an appropriate amount of magnesium ions at the same time. The EA. Hy926 ECs were used to evaluate the biocompatibility of the Mg—P coating prepared in this example, and results showed that a large number of spreading ECs were adhered to the surface of the Mg—P coating and the coating exhibited cytotoxicity reduced from level 2 to level 0, indicating that the Mg—P coating can promote the spreading, adhesion, and proliferation of ECs and significantly improves the cell compatibility of the zinc alloy surface.

Example 8

A biocompatible Mg—P coating was prepared on the surface of an extruded Zn-3 wt % Cu (Zn—Cu) alloy material. The specific steps in this example were basically the same as Example 1 except that:

In step 2), a phosphate reaction solution in this example was prepared specifically as follows: $MgSO_4$ and $NaH_2PO_4$ were taken at a ratio of 5:1 (a ratio of the amounts of the substances, 1 mol/L and 0.2 mol/L, respectively) and dissolved with deionized water, and a pH was adjusted to 4.0 with a 1 mol/L NaOH solution.

In step 3), the treated Zn-3Cu alloy sample was statically soaked in the above phosphate reaction solution for 0.5 h at 80° C. in this example.

It was observed from SEM that the Mg—P coating had a thickness of about 40 μm and a Mg/Zn/P atomic ratio of about 1:2:2. The micro-sized crystal grains on the coating surface had a Mg/P atomic ratio of about 1:1 and basically included no Zn atoms; and there was a bonding force as high as 8 MPa between the coating and the Zn-3Cu alloy matrix. The Mg—P coating prepared in this example, after soaked in a DMEM medium for one week, showed a zinc release rate reduced to 11% of that of a bare Zn-3Cu alloy, and could release an appropriate amount of magnesium ions at the same time. The EA. Hy926 ECs were used to evaluate the biocompatibility of the Mg—P coating prepared in this example, and results showed that a large number of spreading ECs were adhered to the surface of the Mg—P coating and the coating exhibited cytotoxicity reduced from level 2 to level 0, indicating that the Mg—P coating can promote the spreading, adhesion, and proliferation of ECs and significantly improves the cell compatibility of the zinc alloy surface.

Example 9

A biocompatible Mg—P coating was prepared on the surface of an extruded Zn-3 wt % Cu (Zn—Cu) alloy material. The specific steps in this example were basically the same as Example 1 except that:

In step 2), a phosphate reaction solution in this example was prepared specifically as follows: $Mg(NO_3)_2$ and $Na_2HPO_4$ were taken at a ratio of 7:3 (a ratio of the amounts of the substances, 0.35 mol/L and 0.15 mol/L, respectively) and dissolved with deionized water, and a pH was adjusted to 4.0 with a 1 mol/L NaOH solution.

It was observed from SEM that the Mg—P coating had a thickness of about 20 μm and a Mg/Zn/P atomic ratio of about 1:2:2; the micro-sized crystal grains on the coating surface had a Mg/P atomic ratio of about 1:1 and basically included no Zn atoms; and there was a bonding force as high as 8 MPa between the coating and the Zn-3Cu alloy matrix. The Mg—P coating prepared in this example, after soaked in a α-MEM medium for one week, showed a zinc release rate reduced to 12% of that of a bare Zn-3Cu alloy, and could release an appropriate amount of magnesium ions at the same time. The EA. Hy926 ECs were used to evaluate the biocompatibility of the Mg—P coating prepared in this example, and results showed that a large number of spreading ECs were adhered to the surface of the Mg—P coating and the coating exhibited cytotoxicity reduced from level 2 to level 0, indicating that the Mg—P coating can promote the spreading, adhesion, and proliferation of ECs and significantly improves the cell compatibility of the zinc alloy surface.

Example 10

A biocompatible Mg—P coating was prepared on the surface of an extruded Zn-3 wt % Cu (Zn—Cu) alloy material. The specific steps in this example were basically the same as Example 1 except that:

In step 2), a phosphate reaction solution in this example was prepared specifically as follows: $Mg_3(PO_4)_2$ and $KH_2PO_4$ were taken at a ratio of 1:1.5 (a ratio of the amounts of the substances, 0.2 mol/L and 0.3 mol/L, respectively) and dissolved with deionized water, and a pH was adjusted to 4.0 with a 1 mol/L NaOH solution.

It was observed from SEM that the Mg—P coating had a thickness of about 10 μm and a Mg/Zn/P atomic ratio of about 1:2:2; and there was a bonding force as high as 10 MPa between the coating and the Zn-3Cu alloy matrix. The Mg—P coating prepared in this example, after soaked in a α-MEM medium for one week, showed a zinc release rate reduced to 10% of that of a bare Zn-3Cu alloy, and could release an appropriate amount of magnesium ions at the same time. The EA. Hy926 ECs were used to evaluate the biocompatibility of the Mg—P coating prepared in this example, and results showed that a large number of spreading ECs were adhered to the surface of the Mg—P coating and the coating exhibited cytotoxicity reduced from level 2 to level 0, indicating that the Mg—P coating can promote the spreading, adhesion, and proliferation of ECs and significantly improves the cell compatibility of the zinc alloy surface.

Comparative Example 1

A biocompatible Mg—P coating was prepared on the surface of an extruded Zn-3 wt % Cu (Zn—Cu) alloy material. The specific steps in this example were basically the same as Example 1 except that:

In step 2), a phosphate reaction solution in this example was prepared specifically as follows: $KH_2PO_4$ was taken (0.5 mol/L) and dissolved with deionized water, and a pH was adjusted to 4.0 with a 1 mol/L NaOH solution.

Figure 7:
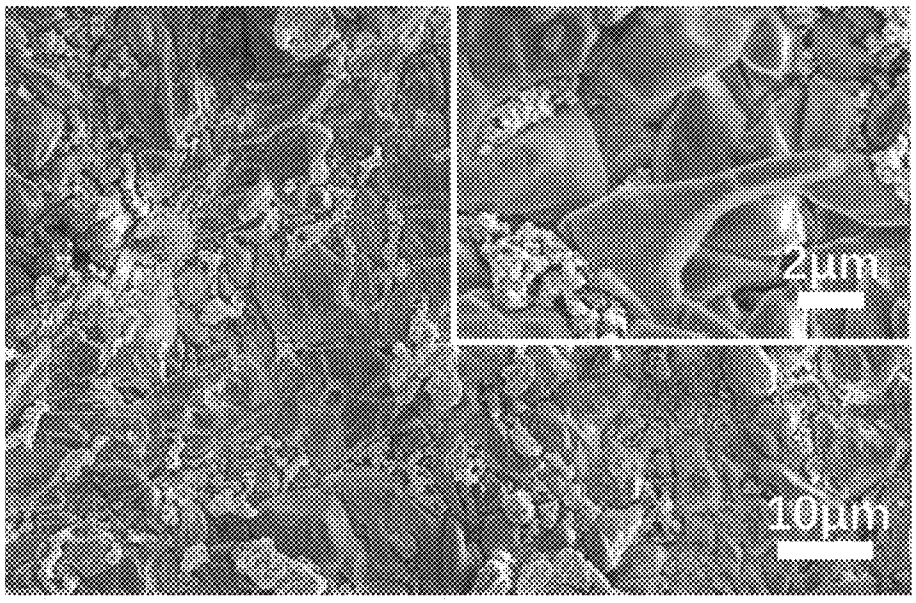
FIG. 7 is an SEM image of the biocompatible Mg—P coating on the surface of a zinc alloy prepared in Comparative Example 1, with an enlarged image at the upper right corner. It can be seen that the coating is not uniform and cannot completely cover the surface of the zinc substrate, and the bare part of the zinc substrate is corroded.

It was observed from SEM (as shown in FIG. 7) that the surface of the substrate was covered with a non-uniform and non-dense coating at a thickness of about 20 μm; the uncovered surface was corroded; a Zn/P atomic ratio was about 3:2 and there was no Mg atoms; and there was a bonding force of 6 MPa between the coating and the Zn-3Cu alloy matrix. The coating prepared in this comparative example, after soaked in a α-MEM medium for one week, showed a zinc release rate basically the same as that of a bare Zn-3Cu alloy. The EA. Hy926 ECs were used to evaluate the biocompatibility of the Mg—P coating prepared in this example, and results showed that a large number of dead ECs were adhered to the coating surface and the coating exhibited cytotoxicity still at levels 1 to 2, without significant improvement.

Comparative Example 2

A biocompatible Mg—P coating was prepared on the surface of an extruded Zn-3 wt % Cu (Zn—Cu) alloy material. The specific steps in this example were basically the same as Example 1 except that:

In step 2), a phosphate reaction solution in this example was prepared specifically as follows: $ZnSO_4$ and $NaH_2PO_4$ were taken at a ratio of 1:1.5 (a ratio of the amounts of the substances, 0.2 mol/L and 0.3 mol/L, respectively) and dissolved with deionized water, and a pH was adjusted to 4.0 with a 1 mol/L NaOH solution.

It was observed from SEM that the surface of the substrate was covered with a non-uniform and non-dense coating at a thickness of about 25 μm. The uncovered surface was corroded; a Zn/P atomic ratio was about 3:2 and there was no Mg atoms; and there was a bonding force of 6 MPa between the coating and the Zn-3Cu alloy matrix. The coating prepared in this comparative example, after soaked in a α-MEM medium for one week, showed a zinc release rate basically the same as that of a bare Zn-3Cu alloy. The EA. Hy926 ECs were used to evaluate the biocompatibility of the Mg—P coating prepared in this example, and results showed that a large number of dead ECs were adhered to the coating surface and the coating exhibited cytotoxicity still at levels 1 to 2, without significant improvement.

There are many ways to specifically apply the present invention, and the above are merely preferred implementations of the present invention. It should be noted that the foregoing examples are provided only for illustrating the present invention and are not intended to limit the protection scope of the present invention. For a person of ordinary skill in the art, several improvements may further be made without departing from the principle of the present invention, and these improvements should also be considered as falling within the protection scope of the present invention.

What is claimed is:

1. A method for preparing a biocompatible Mg—P coating on a surface of a zinc-based biomedical material, the Mg—P biocompatible coating comprises a composite conversion coating of magnesium zinc phosphate and a small amount of zinc phosphate, by adjusting kinetic and thermodynamic conditions, submicron-micron sized magnesium hydrogen phosphate particles are further deposited on the surface of the composite conversion coating, comprising the following steps:

S1. performing a pretreatment on the surface of the zinc-based biomedical material to obtain a pretreated medical zinc alloy, wherein, the pretreatment comprises a polishing, an ultrasonic cleaning, and an ultraviolet (UV)-ozone cleaning; and S2. soaking the pretreated medical zinc alloy obtained in step S1 in an acidic magnesium salt- and phosphate-containing solution at a constant temperature of 10-80° C. for between 2.5 hours to 6 hours, and conducting chemical liquid deposition (CLD) by static soaking of the pretreated medical zinc alloy in the solution to obtain the biocompatible Mg—P coating;

wherein the magnesium salt is selected from the group consisting of magnesium sulfate, magnesium nitrate, and magnesium phosphate; the phosphate is selected from the group consisting of sodium phosphate, disodium hydrogen phosphate, monosodium phosphate, potassium phosphate, dipotassium hydrogen phosphate, and monopotassium phosphate; the concentration of magnesium salt ranges from 0.1 to 1 mol/L, and the concentration of phosphate ranges from 0.15 to 1.5 mol/L; the molar ratio of magnesium salt to phosphate is between 0.5 and 5; the solution containing magnesium salt and phosphate also comprises a solubilizing salt, and the pH of the solution is between 4.0 and 6.2;

in step S2 the solubilizing salt comprises ethylene diamine tetraacetic acid (EDTA).

2. The method for preparing the biocompatible Mg—P coating according to claim 1, wherein the magnesium salt has a concentration of 0.1 to 1 mol/L; the phosphate has a concentration of 0.15 mol/L to 1.5 mol/L; and the magnesium salt and the phosphate have a molar ratio of 0.5:5.

3. The method for preparing the biocompatible Mg—P coating according to claim 1, wherein, in step S2, the soaking is conducted at 10° C. to 80° C. for 4 hours to 5 hours, and the acidic magnesium salt- and phosphate-containing solution has a pH of 4.0 to 6.2.

4. The method for preparing the biocompatible Mg—P coating according to claim 1, wherein the ultrasonic cleaning in step S1 comprises the ultrasonic cleaning successively with absolute ethanol, acetone, and absolute ethanol.

5. A biocompatible Mg—P coating on the surface of the zinc-based biomedical material prepared by the method according to claim 1, wherein the biocompatible Mg—P coating has a thickness of 0.5 μm to 50 μm, the biocompatible Mg—P coating is dense and uniform, and the biocompatible Mg—P coating comprises a main component of zinc-magnesium-phosphate and a predetermined amount of zinc phosphate.

6. The biocompatible Mg—P coating according to claim 5, wherein an outer surface of the biocompatible Mg—P coating further comprises submicro-sized to micro-sized magnesium hydrogen phosphate crystal grains.

7. A method of using a degradable zinc-based biomedical material with the biocompatible Mg—P coating according to claim 5 in a preparation of a biodegradable and absorbable medical device, wherein the biodegradable and absorbable medical device comprises a tissue engineering scaffold, a cardiovascular stent, a medical catheter, and an intraosseous implant device.

8. The method for preparing the biocompatible Mg—P coating according to claim 1, wherein the magnesium salt has a concentration of 0.1 mol/L to 1 mol/L; the phosphate has a concentration of 0.15 mol/L to 1.5 mol/L; and the magnesium salt and the phosphate have a molar ratio of 0.5:5.

* * * * *